(12) United States Patent
Lubitz

(10) Patent No.: US 6,177,083 B1
(45) Date of Patent: Jan. 23, 2001

(54) PROCESS FOR THE PRODUCTION OF VACCINES AND THEIR USE

(75) Inventor: Werner Lubitz, Vienna (AT)

(73) Assignee: Evax Technologies GmbH, Munich (DE)

(*) Notice: Under 35 U.S.C. 154(b), the term of this patent shall be extended for 0 days.

(21) Appl. No.: 08/371,045

(22) Filed: Jan. 10, 1995

Related U.S. Application Data

(63) Continuation of application No. 07/962,226, filed on Jan. 26, 1993, now abandoned.

(30) Foreign Application Priority Data

Jul. 26, 1990 (DE) .................................................. 40 23 721
May 24, 1991 (WO) .................................. PCT/EP91/00967

(51) Int. Cl.[7] .......................... A61K 39/02; A61K 39/00; C12N 1/20
(52) U.S. Cl. .................................... 424/234.1; 424/184.1; 435/252.3; 435/172.3
(58) Field of Search .......................... 435/172.3, 252.3; 424/200.1, 184.1, 234.1, 93.1, 93.2, 93.4

(56) References Cited

U.S. PATENT DOCUMENTS 4,764,370 * 8/1988 Fields et al. ............................ 424/93
4,877,611 * 10/1989 Cantrell ................................... 424/88

FOREIGN PATENT DOCUMENTS

0140864 * 5/1985 (EP) .............................. C12N/15/00

OTHER PUBLICATIONS

Szostak et al. Research in Microbiol. 141: 1005–1007, 1990.*
Lam et al. Current Microbiology 3: 359–64, 1980.*
Henning et al. Proc. Nat. Acad. Sci 70(7): 2033–2036, 1973.*
Levine, "Typhoid Fever Vaccines", In Plotkin SA, Mortimer EA (eds.). Vaccines, WB Saunders Co, Phila, 1988. pp 333–361.*
Berkhout et al EMBO J 4(12): 3315–3320, 1985.*
Manning et al Infect. Immun 53(2): 272–277, 1986.*
Lam et al, Current Microbiology 3:359–364, 1980.*
Wassitik et al, "Tetanus" in *Vaccines* Plotkin et al eds, W.B. Saunders Co., Philadelphia PA, 1988 pp 45–73.*
Witte et al. Eur. J. Biochem 180: 393–398, 1989.*
Clemens et al. J. Infect. Dis 163:1235–1242, 1991.*
Harkness et al, "Construction and Properties of a Chimeric Bacteriophage Lysis Gene." FEMS Microbiology Letters 48 :19–24, 1987.*
Davis et al in *Microbiology* 3rd edition Harper & Row Publishers Philadelphia, 1980 p. 82 & 85.*
Sato et al Bull. Word Health Organ 37(6):973–981, 1967.*
Bryant et al. JAMA 194(1): 123–126, 1965.*
Henrich et al, Mol Gen Genet 185(3): 493–497, 1982.*
Boslego et al, "Gonorrhea Vaccines" in *Vaccines and Immunotherapy* Cryz S. J. ed. Pergamon Press (NY) 1991 p 211–223.*
Cavard et al. J. Mol. Biol. 187: 449–459, 1986.*

\* cited by examiner

*Primary Examiner*—James Housel
*Assistant Examiner*—S. Devi
(74) *Attorney, Agent, or Firm*—Fulbright & Jaworski, LLP

(57) ABSTRACT

Modified bacterium obtainable by transformation of a gram-negative bacterium with the gene of a lytically-active membrane protein from bacteriophages or with the gene of a lytically-active toxin release gene or with genes which contain partial sequences thereof coding for lytic proteins, culturing the bacterium, expression of this lysis gene and isolation of the bacterium modified in this way from the culture broth for use as a vaccine or adjuvant.

12 Claims, 1 Drawing Sheet

PROCESS FOR THE PRODUCTION OF VACCINES AND THEIR USE

This application is a continuation, of application Ser. No. 07/962,226, filed Jan. 26, 1993, now abandoned.

The invention concerns a process for the production of vaccines and their use.

The main purpose of the immunological system in humans and animals is to resist and avoid pathological damage which arises as a result of degenerate cells, infectious viruses, bacteria, fungi or protozoa. A characteristic of the immunological system is that an increasingly stronger resistance occurs after repeated infections with pathogens. The aim of immunization is to build up the power of resistance of the immunological system against certain pathogens without causing corresponding diseases.

Antibodies and cellular T and B lymphocytes are responsible for the specific resistance to pathogens. An important prerequisite for this is the recognition of foreign structures such as e.g. those which occur on a bacterial cell. Depending on the stimulation of the immunological system a temporary or a lifelong immunity to pathogens can be built up by this process after immunization.

It is important for the effectiveness of vaccines that the immune response occurs to a sufficient extent. For this reason it is advantageous to use substances as immunogens which are to a large extent similar in their composition and in their structure to the pathogen against which it is intended to achieve immunity. Thus attenuated or dead bacteria or viruses, processed partial components of pathogens (membrane proteins of bacteria, structural proteins of viruses) or recombinant live vaccines (viruses or bacteria) are used. A disadvantage of using live bacteria or viruses as immunogens is that it is not possible to completely exclude an undesired pathogenic spread of the germs. This danger can be reduced by killing or fragmenting the bacteria and viruses before use as immunogens or vaccines. However, there is a risk that the antigenic determinants will be changed which can lead to a much smaller immune response.

The object of the present invention is therefore to provide immunogens and vaccines against gram-negative bacteria, which can be pathogenic, which do not have these disadvantages.

This object is achieved by a modified bacterium which is obtainable by transformation of a gram-negative bacterium with the gene of a lytically-active membrane protein from bacteriophages or with a lytically-active toxin release gene or with genes which contain partial sequences thereof coding for lytic proteins, culturing the bacterium, expressing this lytic gene, and isolating the bacterium modified in this way from the culture broth. The bacterium is suitable for use as a vaccine or adjuvant.

In the fermentation, the expression of the lytic gene is preferably delayed during the cell growth. This enables an adequate amount of bacteria to be formed first before lysis of these bacteria takes place. The usually impermeable cell wall complex of the bacteria is made permeable in this process such that the cytoplasmic components of the bacteria are released (Eur. J. Biochem. 180 (1989), 393–398). The morphology of the cells, for example, the rod-form of E. coli cells, is preserved. A tunnel structure is merely formed in a localized area of the membrane. The tunnel formation is accompanied by a fusion of the inner and outer membrane at the borders of the tunnel. The modified bacteria formed in this way are hereinafter denoted bacterial ghosts. Bacterial ghosts and their production are described for example in Eur. J. Biochem. 180 (1989) 393–398, Biochimie 72 (1990) 191–200 and J. Bacteriol. 172 (1990) 4109–4114. Their schematic structure is shown in FIG. 1.

The bacterial ghosts consist of a cytoplasmic (inner) membrane, periplasmic space and outer membrane in which the integrity of the cell wall complex is preserved to a large extent. In the case of bacterial strains which have an additional S-layer coat (paracrystalline protein layer outside the outer membrane) this protein layer is also a component of the bacterial ghosts (Ann. Rev. Microbiol. 37 (1983), 311–339).

All gram-negative bacteria, preferably gram-negative pathogens such as those of the genera Neisseria, Escherichia, Bordetella, Campylobacter, Legionella, Pseudomonas, Shigella, Vibrio, Yersinia, Salmonella, Haemophilus, Brucella, Francisella and Bacterioides are suitable as bacteria (Schaechter, M, H. Medoff, D. Schlesinger, Mechanisms of Microbial Disease. Williams and Wilkins, Baltimore (1989)). Examples of pathogenic E. coli strains are: ATCC No. 31618, 23505, 43886, 43892, 35401, 43896, 33985, 31619 and 31617.

The bacterial ghosts are surprisingly well suited as immunogens whereby pronounced cellular and humoral immune responses occur.

A further advantage of the bacterial ghosts according to the present invention is that very many antigenic epitopes of the cell wall complex are presented by the bacterial ghosts. In addition, the lipopolysaccharide present in the bacterial envelope acts as a mitogen and also triggers a signal for cell division. As a result, one achieves an effective stimulation of the B-cell specific production of immunoglobulins.

Lytically-active membrane proteins of bacteriophages are preferably understood as membrane proteins from bacteriophages of the Microviridae class, preferably from icosahedral phages, lytic phages and phages containing ssDNA, which can infect Enterobacteriacae. Examples of these are the phages PhiX174, S13, G4, G6, G14, PhiA, PhiB, PhiC, and PhiR which can infect E. coli C strains. Alpha 3, which can infect E. coli C and E. coli B strains, is also suitable. The phages K9, St-1, PhiK, PhiXtB and U3, which can infect E. coli K12 strains, are also suitable (Sinsheimer R. L. (1968) in: Prog. Nucl. Acid Res. Mol. Biol. (Davidson J. N. & Cohn W. W., eds) Vol.8, Academic Press, New York & London, pp. 115–169; Tessman E. S. & Tessmann I. (1978) in: The single-stranded DNA Phages (Denhardt D. T., Dressler D. & Ray D. S., eds.) Cold Spring Harbor Press, Cold Spring Harbor, pp. 9–29; Hayashi M., Aoyama A., Richardson D. L. & Hayashi M. N. (1987) in: The Bacteriophages, (Calendar R., ed.) Plenum Press, New York, pp. 1–71).

The production of genes, which contain partial sequences of lytic proteins or toxin release genes is preferably carried out according to methods used in genetic engineering via protein engineering, protein design or protein redesign as described for example in D. L. Oxender, C. F. Fox "Protein Engineering" A. R. Liss, Inc. New York, 1987.

In a preferred embodiment, the lytic gene contains the DNA sequence of the E-protein, the N-terminal, membrane-spanning domain of the E-protein, the DNA sequence of the L-protein, the C-terminal, membrane-spanning domain of the L-protein or the DNA sequence of the EL-hybrid protein (sequences cf. EP-A 0 291 021). Partial sequences thereof which act lytically are also suitable. Lytic proteins from the above-mentioned bacteriophages as well as other toxin release genes such as the colicin Lytic gene (Microbiol. Sciences 1 (1984) 168–175 and 203–205) are also preferred as lytically-active membrane proteins.

The invention also provides a process for the production of vaccines which is characterized in that a gram-negative bacterium is transformed with a gene of a lytically-active membrane protein from bacteriophages, with a lytically-active toxin release gene or with genes containing partial sequences thereof which code for lytically-active proteins. The bacterium is cultured, the gene is expressed and subsequently the bacterium modified in this way is isolated from the culture broth. The bacterial ghosts are then preferably purified further from non-lysed bacteria and cell fragments which may be still present, for example by density gradient centrifugation (e.g. with saccharose or ficoll).

The transformation by a vector and the expression of the plasmid-coded genes can be carried out according to processes familiar to one skilled in the art. The transformation is preferably carried out by electroporation or conjugation. Further details on suitable lytic genes and vectors for the transformation, expression and lysis may be found in Witte A. and Lubitz W., Eur. J. Biochem. 180 (1989) 393–398 as well as in the references cited there. Otherwise the preferred embodiments of this process correspond to the preferred embodiments for the vaccines according to the present invention.

During fermentation it is preferable to first inhibit or repress the expression of the lytic gene and then to abolish the inhibition or repression at a desired time, preferably in the late logarithmic phase. An alkaline earth salt such as e.g. magnesium sulphate is preferably added for the inhibition. The preferred concentration range is 0.1–0.6 mol/l.

The invention also provides a process for the production of antibodies which is characterized in that a mammal is immunized with a modified bacterium which is obtainable by transformation of a gram-negative bacterium with the gene of a lytically-active membrane protein from bacteriophages or with a lytically-active toxin release gene or with genes which contain partial sequences thereof which code for lytic protein. The antibodies are isolated, e.g., from the serum or the spleen according to known methods.

In a preferred embodiment, B lymphocytes of the immunized animals are fused with a suitable cell line in the presence of fusing agents. The cell line which produces the desired antibodies is cloned and cultured and the monoclonal antibodies are isolated from the cells or the culture supernatant.

The present invention also concerns the use of the vaccines according to the present invention for the stimulation of T lymphocytes and as an adjuvant.

The present invention also provides a process for the production of vaccines using the bacterial ghosts according to the present invention. The production of these vaccines can be carried out according to the known methods. However, the ghosts are preferably first lyophilised and subsequently suspended, if desired with addition of auxiliary substances.

Furthermore, it is preferred to formulate the vaccine as a multivalent vaccine. For this, the vaccine according to the present invention can be combined with vaccines such as those described in DE 40 05 874.3. A combination with other vaccines familiar to a person skilled in the art is also possible. In this connection, the vaccine according to the present invention can act as a vaccine or as an adjuvant.

In a preferred embodiment, the vaccine is applied as a suspension of bacterial ghosts in an antigen-containing solution. In this connection it is preferred that the antigens are incorporated inside the bacterial ghosts for example by suspending the freeze-dried bacterial ghosts in this antigen-containing solution.

In a further preferred embodiment the vaccine also contains a portion of 0.01% to 5%, preferably 0.01% to 2% and particularly preferably 0.01%–1% live bacteria, with respect to the total amount of bacteria. In this connection it is preferable that the bacteria are from the original strain from which the bacterial ghosts are produced. This strain should in this case be only slightly pathogenic or attenuated (weakened). In addition to the original strain live bacteria of the same species or genus can also be used.

In a further preferred embodiment the bacterial ghosts are mixed with up to 50%, preferably up to 10% bacteria which are approved as live vaccines (e.g. Salmonella and Shigella strains) and used as a vaccine.

The vaccination with the vaccine or vaccine combinations according to the present invention can be carried out according to methods which are familiar to one skilled in the art, for example intradermally, intramuscularly, intraperitoneally, intravenously, subcutaneously and intranasally.

For the intramuscular or subcutaneous administration, the vaccine can for example be suspended in physiological saline. For the intranasal or intra-ocular application the vaccine can for example be applied in the form of a spray or an aqueous solution. For local, for example oral administration it is often necessary to temporarily protect the immunogens against inactivation, for example against saccharolytic enzymes in the cavity of the mouth or against proteolytic enzymes in the stomach. Such a temporary protection can for example be effected by encapsulation of the immunogens. This encapsulation can for example be effected by coating with a protective agent (microencapsulation) or by embedding a multitude of immunogens according to the present invention in a protective carrier (macroencapsulation).

The encapsulation material can be semi-permeable or can become semi-permeable when introduced into the human or animal body. A biologically degradable substance is usually used as the carrier for the encapsulation.

The following examples and the figure elucidate the invention further.

EXAMPLE 1

Fermentation and Lysis

Figure 1A:
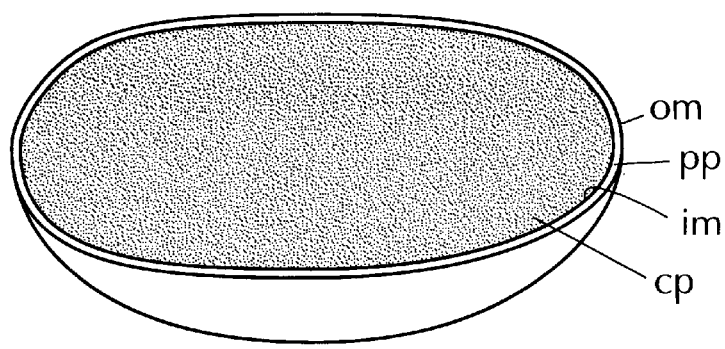
FIG. 1 shows a schematic diagram of a bacterial ghost:
a) longitudinal section through a gram-negative bacterium (om: outer membrane; pp: periplasmic space; im: inner (cytoplasmic) membrane, cp: cytoplasm).
b) Formation of a transmembrane lytic tunnel.
c) Efflux of cytoplasm through the lytic tunnel.
Figure 1B:
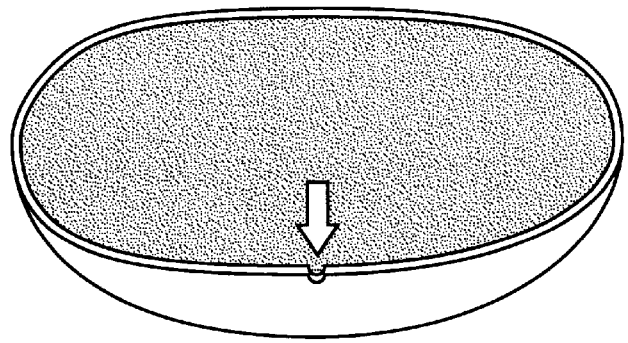
Figure 1C:
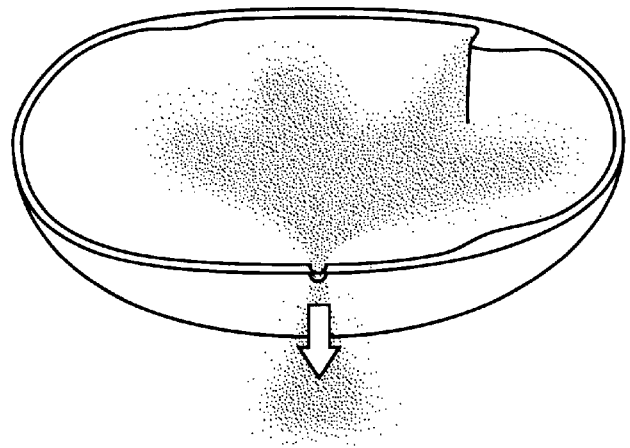

The plasmid pML1 (produced according to DE 40 05 874.3) is integrated into *E. coli* K12 (DSM 2093) and the culture is grown in a shaking flask up to an OD of 0.8–1.2 at 600 nm during which the expression of the lytic gene E is repressed by cI857 repressor molecules (Eur. J. Biochem. 180 (1989) 393 to 398). Gene E is expressed during the exponential growth phase of the bacteria by increasing the temperature to 42° C. which results in thermal inactivation of the cI857 repressor molecules. The lysis of *E. coli* caused by protein E starts between 10 and 30 min after increasing the temperature depending on the culture medium of the bacteria (total medium or minimum medium, under aeration in a shaking water bath). After a further 10 to 30 min the lysis is complete.

Example 2

Modified Protein E-Lysis

The culture is as in Example 1 in which, however, the culture medium is adjusted to 0.2 mol/l magnesium sulphate by adding magnesium sulphate solution 30 min prior to increasing the temperature from 28° C. to 42° C. This prevents the lysis of the bacteria despite the expression of gene E.

The cells are harvested by centrifugation 30 min after increasing the temperature. The cells are lysed instantaneously by resuspending the cell pellet in low molar buffer (PBS, 1 mmol/l phosphate buffer, 1 to 10 mmol/l Tris-HCl pH 6–8) or water. The cell envelopes which are formed during this are denoted bacterial ghosts. Under these conditions, which correspond to a combination of protein E lysis and osmotic shock, a larger lytic structure is obtained in the bacteria. The morphology of the bacterial ghosts is also preserved to a large extent under these conditions.

The bacterial ghosts are washed (resuspension and centrifugation) 2× with PBS or 0.9% NaCl for purification and lyophilized.

Example 3

Immunization

For the immunization $10^9$ lyophilized germs resuspended in 0.9% NaCl (corresponding to 1 mg dry weight bacterial ghosts) are administered intraperitoneally 4× to each mouse at monthly intervals. 8 days after the last immunization serum is obtained and the antibodies are isolated. Antibody titres are obtained against lipopolysaccharide and the outer membrane protein OmpF (J. Biol. Chem. 265 (1990) 6800–6810) which are greater than 1:1000.

In the T-cell proliferation test according to Proc. Natl. Acad. Sci. U.S.A. 85 (1988) 6498–6502 a T-cell stimulation index larger than 20 results.

What is claimed is:

1. A method for eliciting an immune response to a gram-negative bacterium, comprising administering to a mammal an effective amount of an immunogen comprising a gram-negative bacterial ghost, wherein said ghost is characterized by a cytoplasmic membrane, periplasmic space and an outer membrane in which the cell wall complex is preserved to a large extent, said gram-negative bacterial ghost being produced by:
   (a) transforming a gram-negative bacterium with a DNA sequence which encodes a lytically-active membrane protein;
   (b) culturing said transformed gram-negative bacterium to repress expression of said lyrically-active membrane protein; and
   (c) expressing said DNA sequence to produce said lytically-active membrane protein.

2. A method for conferring immunity against a gram-negative bacterium to a mammal, comprising administering to said mammal an effective amount of a vaccine comprising a gram-negative bacterial ghost, wherein said ghost is characterized by a cytoplasmic membrane, periplasmic space and an outer membrane in which the cell wall complex is preserved to a large extent, said gram-negative bacterial ghost being produced by:
   (a) transforming a gram-negative bacterium with a DNA sequence, which encodes a lytically-active membrane protein;
   (b) culturing said gram negative bacterium to express said DNA sequence to produce said lytically active membrane protein; and
   (c) lysing said transformed gram-negative bacterium to produce said gram-negative bacterial ghost.

3. A method according to claim 2, wherein said lytically-active membrane protein is selected from the group consisting of an E-protein, an N-terminal, membrane-spanning domain of said E-protein, an L-protein, a C-terminal, membrane-spanning domain of said L-protein and an EL-hybrid protein.

4. A method according to claim 2 further comprising repressing expression of said DNA sequence for a period of time during said step of culturing followed by ending repression of expression of said DNA sequence during said step of lysing.

5. A method for producing a vaccine of claim 2 further comprising suspending said transformed lytically-active membrane protein producing gram-negative bacterium in an antigen containing solution.

6. A method for enhancing immunity against a gram-negative bacterium in a mammal, comprising administering to said mammal an effective amount of an adjuvant comprising a gram-negative bacterial ghost, wherein said gram-negative bacterial ghost is characterized by an intact cytoplasmic membrane, periplasmic space and an outer membrane in which the cell wall complex is preserved to a large extent, said adjuvant being produced by:
   (a) transforming a gram-negative bacterium with a DNA sequence, which encodes a lytically-active membrane protein;
   (b) culturing said transformed gram-negative bacterium to express said DNA sequence to produce said lytically active membrane protein, and
   (c) lysing said transformed gram-negative bacterium produce said gram-negative bacterial ghost.

7. A method according to claim 2, further comprising mixing said transformed lytically-active membrane protein producing gram-negative bacterium with 0.01%–5% live attenuated bacteria with respect to the total amount of isolated, transformed lytically-active gram-negative bacterium.

8. A method according to claim 2, wherein said transformed producing gram-negative bacterium is mixed with 0.01%–2% live attenuated bacteria with respect to the total amount of transformed lytically-active gram-negative bacterium.

9. A method according to claim 2, wherein said transformed gram-negative bacterium is mixed with 0.01%–1% live attenuated bacteria with respect to the total amount of transformed lytically-active gram-negative bacterium.

10. A method according to claim 1, wherein said lytically-active membrane protein is selected from the group consisting of an E-protein and L-protein.

11. A method according to claim 2, wherein said lytically-active membrane protein is selected from the group consisting of an E-protein and an L-protein.

12. A method according to claim 2, further comprising suspending said gram-negative bacterial ghost in an antigen containing solution.

* * * * *